United States Patent [19]

Cheung et al.

[11] Patent Number: 5,208,405
[45] Date of Patent: May 4, 1993

[54] SELECTIVE HYDROGENATION OF DIOLEFINS

[75] Inventors: Tin-Tack P. Cheung; Marvin M. Johnson, both of Bartlesville, Okla.

[73] Assignee: Phillips Petroleum Company, Bartlesville, Okla.

[21] Appl. No.: 845,128

[22] Filed: Mar. 3, 1992

[51] Int. Cl.$^5$ ............................... C07C 5/05
[52] U.S. Cl. ........................ 585/274; 585/273; 585/260; 585/262
[58] Field of Search ............ 585/273, 274, 260, 262

[56] References Cited

U.S. PATENT DOCUMENTS

| | | | |
|---|---|---|---|
| 2,694,671 | 11/1954 | Baumgarten et al. | 196/36 |
| 2,717,861 | 9/1955 | Baumgarten et al. | 196/36 |
| 3,234,298 | 2/1966 | Langhout et al. | |
| 3,617,518 | 11/1971 | Sinfelt et al. | 585/275 |
| 3,655,621 | 4/1972 | Kasperik et al. | |
| 4,228,088 | 10/1980 | Kuiper | 502/164 |
| 4,404,124 | 9/1983 | Johnson et al. | |
| 4,440,956 | 4/1984 | Couvillion | 585/260 |

*Primary Examiner*—Olik Chaudhuri
*Assistant Examiner*—C. Everhart
*Attorney, Agent, or Firm*—K. K. Brandes

[57] ABSTRACT

A process for selectively hydrogenating $C_4$–$C_{10}$ diolefins to the corresponding monoolefins is carried out with a catalyst comprising (a) nickel metal and/or compound(s), (b) silver metal and/or compound(s), and (c) a solid inorganic support material (preferably alumina).

20 Claims, No Drawings

SELECTIVE HYDROGENATION OF DIOLEFINS

BACKGROUND OF THE INVENTION

This invention relates to the selective hydrogenation of diolefins to monoolefins. In a particular aspect, this invention relates to the removal of diolefins contained in monoolefin streams.

Frequently monoolefin streams, such as those used as feed in polymerization and alkylation reactions, contain diolefins as impurities. These diolefin impurities often interfere with the intended use of the monoolefin(s) and must be substantially removed from the monoolefin streams. A particularly suitable diolefin removal process is the selective hydrogenation of diolefin(s) to the corresponding monoolefin(s) in the presence of catalysts. Frequently, some of these known catalysts are too active and also hydrogenate monoolefins (to paraffins). Other catalysts exhibit too little hydrogenation activity and/or deactivate at an undesirably high rate The present invention pertains to a process for selectively hydrogenating diolefins to monoolefins, wherein the undesirable hydrogenation of monoolefins to paraffins and catalyst deactivation are minimized.

SUMMARY OF THE INVENTION

It is an object of this invention to catalytically hydrogenate diolefins at a high selectivity to monoolefins. It is another object of this invention to selectivity hydrogenate diolefins contained in small amounts in monoolefin streams. Further objects and advantages will be apparent from the detailed description and the appended claims.

In accordance with this invention, a process for hydrogenating at least one diolefin (i.e., alkadiene and/or cycloalkadiene) containing 4–10 carbon atoms per molecule at a high selectivity to at least one monoolefin (i.e., alkene and/or cycloakene) having the same number of carbon atoms per molecule as said at least one diolefin comprises:

contacting a fluid comprising said at least one diolefin and molecular hydrogen with a catalyst composition consisting essentially of (a) at least one nickel promoter selected from the group consisting of nickel metal and readily reducible nickel compounds, (b) at least one silver promoter selected from the group consisting of silver metal and readily reducible silver compounds, and (c) at least one solid inorganic support material, at such contacting conditions as to at least partially (preferably substantially) convert said at least one diolefin to at least one monoolefin (containing the same number of carbon atoms per molecule as said at least one diolefin).

In one preferred embodiment, the at least one diolefin is contained at a level of less than about 3 mole percent in a fluid comprising at least 30 mole percent of at least one monoolefin containing 2–10 carbon atoms per molecule. In a further embodiment, component (c) of the catalyst composition is selected from the group consisting of alumina (presently more preferred), aluminum phosphate, silica, aluminosilicates (clays, zeolites), magnesia, titania, zirconia, hafnia, oxides of lanthanides (such as $La_2O_3$, $CeO_2$, $Sm_2O_3$, Etc.) scandium oxide, yttrium oxide, activated carbon, and mixtures of two or more than two of the above materials.

DETAILED DESCRIPTION OF THE INVENTION

Non-limiting examples of suitable diolefins which can be hydrogenated in the process of this invention include 1,2-butadiene, 1,3-butadiene, isoprene, 1,2-pentadiene, 1,3-pentadiene, 1,2-hexadiene, 1,3-hexadiene, 1,4-hexadiene, 1,5-hexadiene, 2-methyl-1,2-pentadiene, 2-methyl-1,3-pentadiene, 3-methyl-1,3-pentadiene, 2,3-dimethyl-1,3-butadiene, heptadienes, octadienes, monodienes, decadienes, cyclopentadiene, cyclohexadiene, methylcyclopentadienes, cycloheptadienes, methylcyclohexadienes, dymethylcyclopentadienes, ethylcyclopentadienes, octadienes, methylheptadienes, dimethylhexadienes, ethylhexadienes, trimethylpentadienes, methyloctadienes, dimethylheptadienes, ethylheptadienes, trimethylheptadienes, and mixtures of one or two of these diolefins. Presently preferred are diolefins containing 4–6 carbon atoms per molecule.

Non-limiting examples of suitable monolefins which can be present in the feed fluid at a level of at least 30 volume-% include ethylene, propylene, 1-butene, 2-butene, isobutylene, 1-pentene, 2-pentene, methyl-1-butenes (such as 2-methyl-1-butene), methyl-2-butenes (such as 2-methyl-2-butene), 1-hexene, 2hexene, 3-hexene, methyl-1-pentenes (such as 2-methyl-1-pentene), methyl-2-pentenes, 2,3-dimethyl-1-butene, 1-heptene, 2-heptene, 3-heptene, methyl-1-hexenes, methyl-2-hexenes, methyl-3-hexenes, dimethylpentenes, ethylpentenes, octenes, methylheptenes, dimethylhexenes, ethylhexenes, nonenes, methyloctenes, dimethylheptenes, ethylheptenes, trimethylhexenes, cyclopentene, cyclohexene, methylcyclopentenes, cycloheptene, methylcyclohexenes, dimethylcyclopentenes, ethylcyclopentenes, cyclooctenes, methylcycloheptenes, dimethylcyclohexenes, ethylcyclohexenes, trimethylcyclohexenes, methylcyclooctenes, dimethylcyclooctenes, ethylcylcooctenes, and mixtures of two or more than two of these monoolefins. Presently preferred are monoolefins containing 4–6 carbon atoms per molecule.

Generally, the fluid feed (preferably a feed which is gaseous at the hydrogenating conditions of this process) contains less than about 3 mole-% of at least one dioolefin, preferably about 0.05 to about 2.0 mole-% of at least one diolefin. Generally, the fluid feed comprises (preferably consists essentially of) at least one diolefin and at least 30 mole-% of at least one monoolefin, preferably about 50–99.9999 mole-%, more preferably about 90–99.95 mole-%, of at least one monoolefin. However, it is within the scope of this invention (yet presently less preferred) to employ feeds which contain more than 3 mole-% (such as about 3–90 mole-%) of at least one diolefin, or even to employ feeds which consist essentially of at least one diolefin. Also, the feed can contain small amounts (generally less than about 0.1 mole-%) of sulfur compounds (such as mercaptans, organic sulfides) as impurities.

The catalyst composition which is used in the selective hydrogenation process of this invention comprises (a) nickel metal and/or at least one readily reducible Ni compound (such as oxide, nitrate, formate, acetate, and the like); (b) silver metal and/or at least one readily reducible silver compound (such as oxide, nitrate, formate, acetate, and the like), and (c) at least one inorganic support material (listed above; preferably alumina). The term "readily reducible", as used herein, implies that the nickel and silver compounds are converted to the corresponding metals by treatment with hydrogen gas at a temperature of at least 100° C. (preferably at about 100°-450° C.). Suitable aluminas include alpha-alumina, beta-alumina, gamma-alumina, boehmite, diaspore, bayerite and pseudoboehmite.

Generally, the catalyst composition contains about 0.5-10 weight-% Ni and about 1-40 weight-% Ag, at an atomic ratio of Ag:Ni in the range of about 1:1 to about 8:1. Preferably, the catalyst composition contains about 2-5 weight-% Ni and about 8-38 weight-% Ag, at a Ag:Ni atomic ratio of about 2:1 to about 4:1. Generally, the surface area of the catalyst composition (measured by the well-known BET method employing $N_2$) is about 200 to about 300 $m^2/g$, and its average pore volume (as measured by mercury intrusion porosimetry, as described in U.S. Pat. No. 4,975,399, Column 2) is about 0.2 to about 0.3 cc/g. The catalyst particles can have any suitable shape (such as spherical cylindrical, granular, trilobal and the like) and any suitable size (such as an average spherical pellet diameter of about 1-5 mm min).

The catalyst particles used in the process of this can be prepared in any suitable manner. Preferably, the support material is impregnated with at least one nickel compound and at least one silver compound (either simultaneously or sequentially in any order), followed by drying (preferably at about 80°-120° C., for about 0.1-10 hours) and calcining (preferably at about 400°-500° C., for about 0.5-10 hours in air or in an inert gas atmosphere).

The calcined catalyst can be employed directly in the selective hydrogenation process of this invention. However, it is preferred to heat the catalyst in a reducing gas such as hydrogen since optimum operation of the selective hydrogenation does not begin until there has been a substantial reduction of the catalytic metals. Typically, the reduction is carried out at a temperature in the range of about 100° C. to about 450° C. for at least 10 minutes (preferably about 1-10 hours.

The selective hydrogenation is generally carried out by contacting a gas stream containing at least one diolefin and molecular hydrogen with the catalyst (generally contained in a fixed bed). Generally, at least one mole of hydrogen is employed for each mole of diolefin. Preferably, the process of this invention employs about 3-10 moles $H_2$ per mole diolefin.

The temperature necessary for the selective hydrogenation process of this invention depends largely upon the activity of the catalyst and the desired extent of diolefin hydrogenation. Generally, temperatures in the range of about 35° C. to about 200° C. are used. Any suitable reaction pressure can be employed. Generally, the total pressure is in the range of about 50 to 1,000 pounds per square inch gauge (psig). The gas hourly space velocity (GHSV) of the hydrocarbon feed can also vary over a wide range. Typically, the space velocity will be in the range of about 1,000 to about 10,000 liters of hydrocarbon feed per liter of catalyst per hour, more preferably about 2,000 to about 8,000 liter/liter/hour. The hydrogenation process conditions should be such as to avoid significant hydrogenation of monoolefins (formed by hydrogenation of diolefins and/or being initially present in the feed).

Regeneration of the catalyst may be accomplished by heating the catalyst in air at a temperature preferably not in excess of 500° C. to burn off any organic matter, polymer or char. The regenerated catalyst can be reemployed in the selective hydrogenation process of this invention, generally after reduction with hydrogen, as described above.

The process of this invention will be further illustrated by the following non-limiting examples.

EXAMPLE I

This example illustrates the preparation of supported nickel and/or silver catalyst which were used for catalyzing the selective hydrogenation of diolefins.

Catalyst A (Control) was a $Ni/Al_2O_3$ material containing about 5 weight percent Ni. Catalyst A was prepared by impregnating 40.06 g of 10-20 mesh S-201 alumina (provided by Aluminum Company of America, Pittsburgh, Pa.) with a solution of 9.85 g $Ni(NO_3)_2 \cdot 6H_2O$ in 30 mL water. The thus-impregnated alumina was dried overnight at about 71° C. in a circulating air oven, and was then calcined in air for about 5 hours at 500° C.

Catalyst B (Control) was an $Ag/Al_2O_3$ material containing about 24 weight-% Ag. Catalyst B was prepared by impregnating 40.06 g of 10-20 mesh S-201 alumina with a solution of 23.66 g of $AgNO_3$ in 30 mL $H_2O$. The thus-impregnated material was dried and calcined, as described for Catalyst A.

Catalyst C (Invention) was an $Ag/Ni/Al_2O_3$ material containing about 24 weight-% Ag and about 5 weight-% Ni. Catalyst C was prepared by impregnating 34.7 g of 10-20 mesh S-201 alumina with an aqueous solution containing 9.77 g $Ni(NO_3)_2 \cdot 6H_2O$ and 23.63 g $AgNO_3$ in 30 mL $H_2O$. The thus-impregnated material was dried and calcined, as described for Catalyst A.

EXAMPLE II

This example illustrates the performance of alumina-supported Ni, Ag and Ni/Ag catalysts in the selective hydrogenation of diolefins contained in a $C_5+$ gasoline fraction. About 20 cc of each of the catalysts described in Example I was placed in a stainless steel reactor tube having a 0.5 inch inner diameter. Each catalyst was reduced in flowing hydrogen gas (introduced in a downflow mode at a rate of about 40 cc/minute) for about 6 hours at a temperature of about 370° C. and a pressure of about 100 psig). Thereafter, the reactor was allowed to cool to about 40° C. in a stream of flowing $H_2$ gas. Then a liquid $C_5+$ gasoline fraction was introduced into the reactor in a downflow mode at a rate of about 1 cc/minute. The hydrogen gas flow was adjusted to about 10-20 cc/minute, and the total reaction pressure was adjusted to about 200 psig. Samples of the hydrogenated product were analyzed by means of gas chromatography at intervals of about 1-2 hours. The most pertinent test results for each catalyst are summarized in Tables I, II and III.

TABLE I

| Catalyst | Reaction Temp (°C.)[1] | Wt % in Product $C_5$ Diolefins[2] | Wt % in Product $C_5$ Monoolefins | % Removal of $C_5$ Diolefins |
|---|---|---|---|---|
| None (Feed) | — | 1.32 | 44.2 | — |
| A ($Ni/Al_2O_3$) | 44 | 0.67 | 42.4 | 50 |
|  | 48 | 0.12 | 38.7 | 91 |
|  | 71 | 0.36 | 42.3 | 73 |
|  | 75 | 0.29 | 39.3 | 78 |
|  | 93 | 0.19 | 43.9 | 86 |
|  | 96 | 0.23 | 42.0 | 83 |
|  | 111 | 1.05 | 44.7 | 21 |
|  | 136 | 1.19 | 44.6 | 11 |
| $A^3$ ($Ni/Al_2O_3$) | 46 | 0.83 | 43.3 | 38 |
|  | 89 | 0 | 38.4 | 100 |
|  | 106 | 0 | 39.7 | 100 |
|  | 117 | 0 | 42.6 | 100 |
|  | 130 | 0 | 44.1 | 100 |

TABLE I-continued

| Catalyst | Reaction Temp (°C.)[1] | Wt % in Product | | % Removal of $C_5$ Diolefins |
|---|---|---|---|---|
| | | $C_5$ Diolefins[2] | $C_5$ Monoolefins | |
| Catalyst was reactivated with $H_2$ | | | | |
| | 54 | 0.49 | 45.2 | 63 |
| | 63 | 0.27 | 44.9 | 80 |
| | 72 | 0.15 | 45.0 | 89 |
| | 82 | 0.10 | 48.9 | 92 |
| | 91 | 0.07 | 45.0 | 95 |
| | 105 | 0.07 | 45.0 | 95 |
| | 120 | 0.25 | 45.1 | 81 |
| | 152 | 1.26 | 45.4 | 5 |
| | 179 | 1.25 | 45.2 | 5 |

[1]measured in the center of the reactor
[2]mainly 2-methyl-1,3-butadiene and 1,3-pentadiene
[3]second fresh sample of Catalyst A Test data in Table I indicate that the $Ni/Al_2O_3$ catalyst was generally too active at the beginning of each run resulting in undesirable hydrogenation of monoolefins. Furthermore, the catalyst had a tendency to rapidly deactivate at higher temperatures.

TABLE II

| Catalyst | Reaction Temp (°C.)[1] | Wt % in Product | | % Removal of $C_5$ Diolefins |
|---|---|---|---|---|
| | | $C_5$ Diolefins[2] | $C_5$ Monoolefins | |
| None (Feed) | — | 1.29 | 43.8 | |
| B ($Ag/Al_2O_3$) | 67 | 1.28 | 45.5 | 1 |
| | 93 | 0.99 | 45.3 | 23 |
| | 133 | 0.55 | 45.8 | 57 |
| | 155 | 0.27 | 46.0 | 77 |
| | 176 | 0.03 | 46.2 | 98 |
| | 196 | 0.07 | 46.1 | 95 |
| | 197 | 0 | 45.9 | 100 |

[1]See Table I
[2]See Table II

Test data in Table II indicate that the $Ag/Al_2O_3$ catalyst was sufficiently active and selective (to diolefin hydrogenation) only at relatively high temperatures (155° C. and higher).

TABLE III

| Catalyst | Reaction Temp (°C.)[1] | Wt % in Product | | % Removal of $C_5$ Diolefins |
|---|---|---|---|---|
| | | $C_5$ Diolefins[2] | $C_5$ Monoolefins | |
| None (Feed) | — | 1.21 | 44.1 | — |
| C ($Ag/Ni/Al_2O_3$) | 32 | 0.66 | 44.6 | 45 |
| | 61 | 0.05 | 43.0 | 96 |
| | 62 | 0.17 | 43.8 | 86 |
| | 80 | 0.15 | 43.4 | 88 |
| | 91 | 0.04 | 43.4 | 97 |
| | 92 | 0.02 | 43.2 | 98 |
| | 101 | 0.02 | 43.4 | 98 |
| | 101 | 0.02 | 45.5 | 98 |
| | 110 | 0.03 | 43.5 | 97 |
| | 110 | 0.02 | 43.6 | 98 |
| | 110 | 0.01 | 44.0 | 99 |
| | 112 | 0.01 | 43.5 | 99 |
| | 120 | 0.02 | 44.1 | 98 |
| | 120 | 0.04 | 43.9 | 96 |
| | 134 | 0 | 44.8 | 100 |
| | 134 | 0 | 45.3 | 100 |
| | 158 | 0 | 44.2 | 100 |
| | 158 | 0 | 45.3 | 100 |
| | 133 | 0.04 | 45.3 | 97 |
| | 133 | 0.04 | 45.4 | 97 |
| | 158 | 0 | 45.7 | 100 |
| | 158 | 0.02 | 45.8 | 98 |
| | 163 | 0.03 | 45.6 | 97 |
| | 174 | 0 | 45.5 | 100 |

[1]See Table I
[2]See Table I

Test data in Table III clearly show that the $Ag/Ni/Al_2O_3$ catalyst of this invention was quite active for catalyzing the hydrogenation of diolefins at relatively low temperatures (as low as about 60° C.), without significant monoolefin hydrogenation. No appreciable catalyst deactivation was observed after almost 3 days on stream. Thus, this catalyst did not exhibit the earlier described disadvantages of the $Ni/Al_2O_3$ and $Ag/Al_2O_3$ catalysts.

Reasonable variations and modifications which will be apparent to those skilled in the art, can be made within the scope of the disclosure and appended claims without departing from the scope of this invention.

That which is claimed is:

1. A process for hydrogenating at least one diolefin containing 4–10 carbon atoms per molecule at a high selectivity to at least one monoolefin having the same number of carbon atoms per molecule as said at least one diolefin which comprises:

contacting a fluid feed comprising said at least one diolefin and molecular hydrogen with a catalyst composition consisting essentially of (a) at least one nickel promoter selected from the group consisting of nickel metal and readily reducible nickel compounds, (b) at least one silver promoter selected from the group consisting of silver metal and readily reducible silver compounds, and (c) at least one solid inorganic support material, wherein said process is carried out at a temperature in the range of about 35° C. to about 200° C. so as to at least partially convert said at least one diolefin to said at least one monoolefin.

2. A process in accordance with claim 1, wherein said fluid feed contains said at least one diolefin at a level of about 0.05 to about 2.0 mole percent.

3. A process in accordance with claim 1, wherein said fluid feed further comprises at least about 30 mole percent of at least one monoolefin containing 2–10 carbon atoms per molecule.

4. A process in accordance with claim 1, wherein said fluid feed is a gas and said at least one diolefin contains 4–6 carbon atoms per molecule.

5. A process in accordance with claim 1, wherein component (a) of said catalyst composition contains at least one material selected from the group consisting of nickel metal, nickel oxide, nickel nitrate, nickel formate and nickel acetate.

6. A process in accordance with claim 5, wherein component (b) of said catalyst composition is at least one material selected from the group consisting of silver metal, silver oxide, silver nitrate, silver formate and silver acetate.

7. A process in accordance with claim 6, wherein component (c) of said catalyst composition is selected from the group consisting of alumina, aluminum phosphate, silica, aluminosilicates, magnesia, titania, zirconia, hafnia, oxides of lanthanides, scandium oxide, yttrium oxide and activated carbon.

8. A process in accordance with claim 7, wherein said component (c) is alumina.

9. A process in accordance with claim 7, wherein said catalyst composition contains about 0.5–10 weight percent nickel and about 1–40 weight percent silver, at an atomic ratio of silver to nickel in the range of about 1:1 to about 8:1.

10. A process in accordance with claim 9, wherein component (c) of said catalyst composition is alumina.

11. A process in accordance with claim 9, wherein said catalyst composition has a surface area of about 200–300 m$^2$/g and an average pore volume of about 0.2–0.3 cc/g.

12. A process in accordance with claim 9, wherein said catalyst composition has been activated by heating with molecular hydrogen at a temperature of about 100° C. to about 450° C. for at least 10 minutes.

13. A process in accordance with claim 1, wherein said process employs about 3–10 moles of molecular hydrogen per mole of said at least diolefin present in said fluid feed.

14. A process in accordance with claim 13, wherein said fluid feed is a gas and said at least one diolefin contains 4–6 carbon atoms per molecule.

15. A process in accordance with claim 14, wherein said fluid feed contains at least about 30 mole percent of at least one monoolefin containing 2–10 carbon atoms.

16. A process in accordance with claim 13, wherein said process is carried out at a pressure of about 50–1,000 psig.

17. A process for hydrogenating at least one diolefin containing 4–10 carbon atoms per molecule at a high selectivity to at least one monoolefin having the same number of carbon atoms per molecule as said at least one diolefin which comprises:

contacting a fluid feed comprising said at least one diolefin and molecular hydrogen with a catalyst composition consisting essentially of (a) at least one nickel promoter selected from the group consisting of nickel metal and readily reducible nickel compounds, (b) at least one silver promoter selected from the group consisting of silver metal and readily reducible silver compounds, and (c) at least one solid inorganic support material, wherein the atomic ratio of silver to nickel in said catalyst composition is in the range of about 1:1 to about 8:1 and said process is carried out at a temperature in the range of about 35° C. to about 200° C., so as to at least partially convert said at least one diolefin to said at least one monoolefin.

18. A process in accordance with claim 17, wherein component (a) of said catalyst composition contains at least one material selected from the group consisting of nickel metal, nickel oxide, nickel nitrate, nickel formate and nickel acetate;

component (b) of said catalyst composition is at least one material selected from the group consisting of silver metal, silver oxide, silver nitrate, silver formate and silver acetate; and component (c) of said catalyst composition is selected from the group consisting of alumina, aluminum phosphate, silica, aluminosilicates, magnesia, titania, zirconia, hafnia, oxides of lanthanides, scandium oxide, yttrium oxide and activated carbon.

19. A process in accordance with claim 17, wherein said catalyst composition contains about 0.5–10 weight percent nickel and about 1–40 weight percent silver.

20. A process in accordance with claim 17, wherein said fluid feed is a gas and said at least one diolefin contains 4–6 carbon atoms per molecule.

* * * * *